United States Patent [19]

Daum et al.

[11] 4,034,104

[45] July 5, 1977

[54] CARBAMIC ACID ESTERS OF GALLIC ACID, THEIR ESTERS, AND HEAVY METAL SALTS

[75] Inventors: Werner Daum, Krefeld; Wilhelm Brandes, Cologne; Paul-Ernst Frohberger, Leverkusen, all of Germany

[73] Assignee: Bayer Aktiengesellschaft, Leverkusen, Germany

[22] Filed: June 10, 1976

[21] Appl. No.: 694,861

[30] Foreign Application Priority Data

July 3, 1975 Germany .................... 2529648

[52] U.S. Cl. .................... 424/289; 260/429.9; 260/465 D; 260/471 C; 424/288; 424/295; 424/300
[51] Int. Cl.[2] .................... C07F 3/06; A01N 9/20
[58] Field of Search .......... 424/289, 300, 288, 295; 260/471 C, 429.9, 465 D

[56] References Cited

UNITED STATES PATENTS

| | | | |
|---|---|---|---|
| 1,889,383 | 11/1932 | Schmidt | 260/429.9 X |
| 2,716,659 | 8/1955 | Kreysa et al. | 260/471 C |
| 2,787,621 | 4/1957 | Hook et al. | 260/429.9 X |
| 3,808,261 | 4/1974 | Ruschig et al. | 424/308 |

*Primary Examiner*—Dale R. Ore
*Attorney, Agent, or Firm*—Burgess, Dinklage & Sprung

[57] ABSTRACT

Carbamic acid esters of gallic acid, their esters, and heavy metal salts of the formula

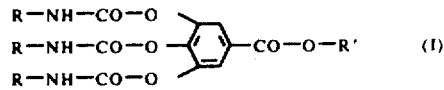

in which
R represents alkyl with up to 8 carbon atoms, which alkyl group can be substituted by halogen or cyano groups, and
R' represents hydrogen, optionally halogen-substituted alkyl with up to 6 carbon atoms or one equivalent of a heavy metal atom, which possess fungicidal properties.

8 Claims, No Drawings

CARBAMIC ACID ESTERS OF GALLIC ACID, THEIR ESTERS, AND HEAVY METAL SALTS

The present invention relates to and has for its objects the provision of particular new carbamic acid esters of gallic acid, their esters, and heavy metal salts which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

As has already been known for a long time, zinc ethylene-1,2-bis-dithiocarbamate (Compound A) and N-trichloromethylthiotetrahydrophthalimide (Compount B) can be used as fungicides in agriculture and in horticulture; the compounds mentioned are of great importance among commercially available products (see R. Wegler, "Chemie der Pflanzenschutzund Schadlingsbekampfungsmittel" ("Chemistry of Plant Protection Agents and Pesticides"), Volume 2, pages 65 and 108, Berlin/Heidelberg/New York (1970)). However, the action is not always satisfactory if low concentrations are used. In addition, active compounds from the group of the carbamic acid phenyl esters have already been described for use in the agricultural field. In the case of some of these active compounds, their use as insecticides is predominant (see, for example, British Patent Specification No. 1,099,084). Carbamic acid phenyl esters having a fungicidal action are also known; these compounds are in most cases nuclear-halogenated (see, for example, German Published Specification DOS 1,668,085). Their activity is also unreliable if low amounts are used, and at higher concentrations damage to the plants is observed not infrequently.

The present invention now provides, as new compounds, the carbamic acid esters of gallic acid, their esters and their heavy metal salts, of the general formula

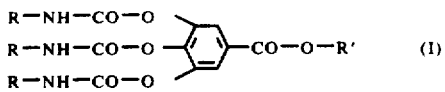

in which
R is alkyl with up to 8 carbon atoms optionally substituted by halogen or cyano, and
R' is hydrogen, optionally halogen-substituted alkyl with up to 6 carbon atoms or one equivalent of a heavy metal atom.

Preferably R is alkyl with up to 6 carbon atoms, which may be substituted by cyano or chlorine (ω-cyanopentyl being an especially preferred meaning for R), and R' is hydrogen, straight-chain or branched alkyl with up to 6 carbon atoms, which may optionally carry 1 to 3 substituents selected from fluorine and chlorine atoms, or one equivalent of a zinc (II), tin (II), manganese (II), iron (II), iron (III), cobalt (II) or nickel (II) atom, It is totally surprising that the carbamic acid esters of gallic acid, according to the invention, exhibit a greater fungicidal action than the compounds known from the state of the art. The use of the compounds according to the invention also has advantages in respect of toxicology and toleration by plants, since one of the components, namely gallic acid, is a compound which is widely encountered in the plant kingdom, and is harmless. In addition, the deficiency diseases of crop plants encountered in some areas can, to some degree, be counteracted with the heavy metal salts of iron, manganese and/or zinc that are within the scope of the present invention. The compounds according to the invention thus represent a valuable enrichment of the art.

The invention also provides a process for the preparation of a compound of the formula (I) in which gallic acid or a derivative of gallic acid, of the general formula

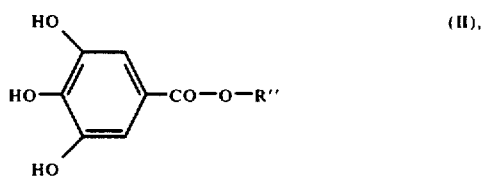

in which
R" is hydrogen or alkyl with up to 6 carbon atoms, which alkyl radical can be substituted by halogen, is reacted with an isocyanate of the general formula

in which
R has the above-mentioned meaning,
in the presence of a base and, if appropriate, in the presence of an inert solvent, and, if required, the free acid (wherein R' in the formula (I) represents hydrogen) is prepared by subsequent acidification with mineral acid, and this free acid, if furthermore required (in order to prepare those compounds of the formula (I), in which R' represents heavy metal), is reacted with a heavy metal salt in the presence of a strong base.

If ω-cyanopentyl isocyanate, gallic acid, triethylamine, sulphuric acid, sodium hydroxide solution and zinc sulphate are used as the starting materials, the reaction sequence can be represented by the following formula scheme;

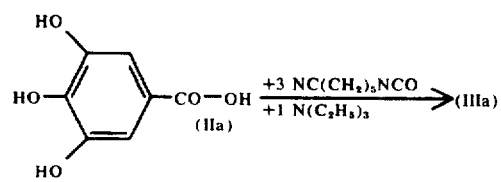

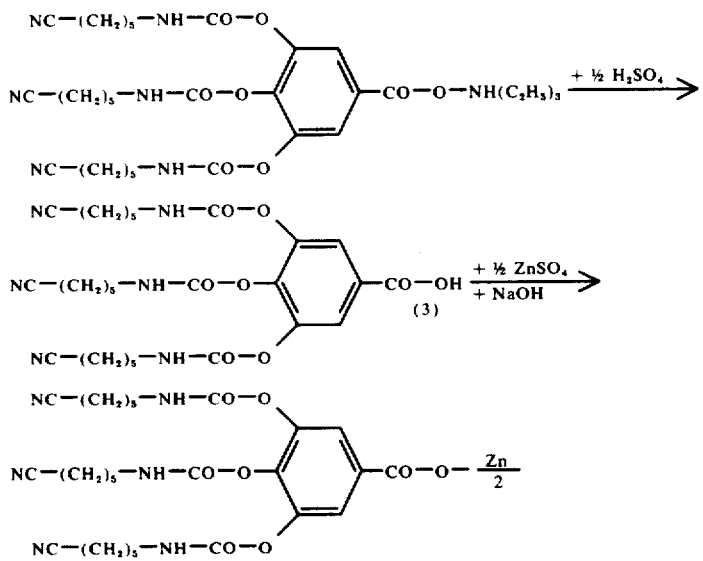

-continued

Gallic acid and its simple derivatives are generally known. The following may be mentioned as particularly preferred examples of the starting materials of the formula (II): gallic acid and gallic acid methyl, ethyl, propyl, butyl, isobutyl, pentyl, isopentyl and hexyl esters.

The isocyanates of the formula (III) which are also required as starting materials are already known. The following may be mentioned as examples: methyl, ethyl, propyl, isopropyl, butyl, isobutyl, sec.-butyl, pentyl, 1-ethyl-propyl, hexyl, 1,2,2-trimethyl-propyl, α-methylisobutyl, ω-cyanoethyl, ω-chloroethyl and ω-chlorohexyl isocyanates.

As diluents for carrying out the reaction according to the invention it is possible to use all solvents which are inert towards isocyanates. These include, for example, chlorinated hydrocarbons, such as methylene chloride, ethylene chloride and chloroform, and also toluene, xylene, dimethylformamide and dimethylacetamide.

As bases required for carrying out the reaction it is preferred to use tertiary amines. The procedure to be employed is generally as follows: the gallic acid ester or gallic acid and approximately the stoichiometric amount of the amine, for example triethylamine, benzyldimethylamine, cyclohexyldimethylamine, dodecyldimethylamine, pyridine or picoline, are initially introduced into an inert solvent.

If gallic acid is used as the starting material, it is also possible to proceed by first preparing an anhydrous alkali metal salt of this acid. If, on the other hand, a gallic acid alkyl ester is used as the starting material, the presence of a catalytic amount of the tin salt of a long-chain carboxylic acid or of triethylenediamine or of some other suitable amine suffices. In the latter case, the reaction can also be carried out in the absence of a solvent.

The reaction temperatures can be varied within a fairly wide range. In general, the reaction is carried out at between $-20°$ and $+120°$ C, preferably at from $30°$ to $90°$ C. It is best to add the isocyanate component to the reaction mixture in such a way that the strongly exothermic carbamate formation can be controlled.

In carrying out the process according to the invention, 3 to 4 moles of isocyanate are generally employed per mole of gallic acid or gallic acid ester, but it is also possible to use up to about 20% less or more than this range without a significant reduction in yield.

The tris-carbamoyl-gallic acid alkyl esters crystallize out on treatment with less polar solvents, for example with toluene, xylene or dibutyl ether. The free tris-carbamoyl-gallic acids are sparingly soluble and separate out after addition of water and a strong acid, such as sulphuric acid, phosphoric acid, toluenesulphonic acid or benzenesulphonic acid, to the reaction mixture, while cooling to a temperature of, preferably, $0°$ to $+10°$ C. They are separated off by suitable measures, such as suction filtration or centrifugation, washed with water until free from salt and dried in vacuo.

Those compounds of the formula (I), in which R' represents one equivalent of a heavy metal atom, are generally obtained as follows: the tris-carbamoyl-gallic acids are suspended in a two-phase mixture of water and an inert organic solvent, such as chloroform, ethylene chloride, toluene or, preferably, methylene chloride, and a slight excess of a water-soluble heavy metal salt is added at a temperature of, preferably, $0°$ to $+10°$ C. A stronger base which does not form complexes, such as sodium hydroxide solution, potassium hydroxide solution or even sodium carbonate is added slowly while thoroughly agitating the multi-phase mixture. If the tris-carbamoyl-gallic acids go into solution, the organic phases obtained are washed thoroughly with water in the cold, dried over sodium sulphate and concentrated in vacuo. The residual solvent is removed from the resulting viscous residues by vacuum drying at about $50°$ C. If the resulting heavy metal salts are sparingly soluble in the organic solvent, they can be separated off by suction filtration.

With regard to definition, it should still be noted that in the present context "heavy metals" are usually understood as those metals which have a specific gravity above $5g/cm^3$. Examples which may be mentioned here are: zinc, copper, cadmium, tin, manganese, iron, cobalt and nickel.

The active compounds according to the invention, as already mentioned, exhibit a powerful fungitoxic action and are distinguished by a broad spectrum of action. Their low toxicity to warm-blooded animals and their good toleration by higher plants permits their use as plant protection agents against fungal diseases. They do not harm crop plants in the concentrations required for combating the fungi. Fungi-toxic agents are employed in plant protection for combating fungi from the most diverse classes of fungi, such as *Archimycetes, Phycomycetes, Ascomycetes, Basidiomycetes* and *Fungi Imperfecti.*

The active compounds according to the invention can be employed against parasitic fungi or aerial parts of plants, fungi which cause tracheomycosis and which attack the plant through the soil, seed-borne fungi and soil-inhabitating fungi. The following may be mentioned individually as important fungi to be combated with the compounds according to the invention: species of *Phytophthora*, species of *Venturia* and fungi responsible for rust diseases.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g., cyclohexane, etc.), paraffins (e.g. petroleum or mineral oil fractions), chlorinated aliphatic hydrocarbons (e.g., methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.) and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

In addition to the above formulation possibilities it should be noted that the compounds according to the invention can be formulated together with sucrose, dextrose, dextrins, anhydrous calcium sulphate or calcium sulphate hemihydrate.

In practice it can be of advantage to add heavy metal salts to the formulations of the tris-carbamoyl-gallic acids or tris-carbamoyl-gallic acid alkyl esters.

Such active compounds may be employed alone or in the form of mixtures with one another and/or with such solid and/or liquid dispersible carrier vehicles and/or with other known compatible active agents, especially plant protection agents, such as other fungicides, or nematocides, insecticides, acaricides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90%, of the mixture.

If aqueous active compound preparations are used the active compound concentrations can vary within wider ranges and in that case are usually from 0.0005 to 2.0% by weight.

Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. a fungicidally effective amount, of the particular active compound of the invention along or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

*Phytophthora* test (tomatoes)/protective
Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20° C and at a relative atmospheric humidity of 70%. The tomato plants were then inoculated with an aqueous spore suspension of *Phytophthora infestans*. The plants were brought into a moist chamber with an atmospheric humidity of 100% and a temperature of 18°–20° C.

After 5 days the infection of the tomato plants was determined. The assessment data were converted to per cent infection: 0% means no infection; 100% means that the plants were totally infected.

The active compound, the concentrations of the active compound and the results can be seen from the following table:

Table 1

*Phytophthora* test (tomatoes)/protective

| Active compound | Infection in % at an active compound concentration of 0.0062% | 0.0031% |
|---|---|---|
| (A) (known) Zn dithiocarbamate structure | 59 | 83 |
| (1) Trihydroxy benzoic acid tris-cyanoalkylcarbamate | 10 | 35 |
| (3) Zn salt derivative | 22 | 61 |
| (2) n-propyl ester derivative | 45 | 65 |
| (6) Fe(III) salt derivative | 29 | 57 |

Table 1-continued

| | Phytophthora test (tomatoes)/protective | |
|---|---|---|
| | | Infection in % at an active compound concentration of |
| Active compound | 0.0062% | 0.0031% |
| NC(CH$_2$)$_5$—NH—CO—O— (benzene ring with three NC(CH$_2$)$_5$—NH—CO—O— substituents and —CO—O—Fe(II)/2 group) (7) | 15 | 54 |

EXAMPLE 2

*Fusicladium* test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were sprayed with the spray liquid until dripping wet. The plants remained in a greenhouse for 24 hours at 20° C and at a relative atmospheric humidity of 70%. They were then inoculated with an aqueous conidium suspension of the apple scab causative organism (*Fusicladium dendriticum*) and incubated for 18 hours in a humidity chamber at 18°–20° C and at a relative atmospheric humidity of 100%.

The plants were then brought into a greenhouse for 14 days.

15 days after inoculation, the infection of the seedlings was determined. The assessment data were converted to per cent infection. 0% means no infection; 100% means that the plants were totally infected.

The active compounds, the concentrations of the active compounds and the results can be seen from the following table:

Table 2

| | Fusicladium test (apple)/protective |
|---|---|
| | Infection in % at an active compound concentration of 0.0025% |
| Active compound | |
| Phthalimide with N—S—CCl$_3$ group (known) (B) | 42 |
| NC—(CH$_2$)$_5$—NH—CO—O— (benzene ring trisubstituted with NC—(CH$_2$)$_5$—NH—CO—O— groups and —CO—OH) (1) | 21 |
| NC—(CH$_2$)$_5$—NH—CO—O— (benzene ring trisubstituted with NC—(CH$_2$)$_5$—NH—CO—O— groups and —CO—O—Zn/2) (3) | 17 |
| NC—(CH$_2$)$_5$—NH—CO—O— (benzene ring trisubstituted with NC—(CH$_2$)$_5$—NH—CO—O— groups and —CO—O—Fe(III)/3) (6) | 21 |

Table 2-continued

| Fusicladium test (apple)/protective | |
|---|---|
| Active compound | Infection in % at an active compound concentration of 0.0025% |
| NC—(CH₂)₅—NH—CO—O— benzene ring with three such substituents and —CO—O—Mn(II)/2 (9) | 10 |

EXAMPLE 3

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C and 100% relative atmospheric humidity.

After 10 days' dwell time of the plants at a temperature of 20° C and 80–90% atmospheric humidity, the occurrence of rust pustules on the plant was evaluated. The degree of infection was expressed as a percentage of the infection of the untreated control plants. 0% denotes no infection and 100% denotes the same degree of infection as in the case of the untreated control. The active compound was the more active, the lower was the degree of rust infection.

The active compounds, active compound concentrations in the spray liquor and degrees of infection can be seen from the table which follows:

Table 3

| Shoot treatment test/cereal rust/protective | | |
|---|---|---|
| Active compounds | Active compound concentration in the spray liquor in % by weight | Infection in % of the untreated control |
| untreated | — | 100 |
| CH₃—NH—C(=S)—S\ Zn /S—C(=S)—NH—CH₃ (A) (known) | 0.025 | 93.8 |
| | 0.01 | 100 |
| | 0.005 | 100 |
| | 0.0025 | 100 |
| NC—(CH₂)₅—NH—CO—O— (trisubstituted benzene) —CO—O—C₃H₇-n (2) | 0.025 | 32.5 |
| NC—(CH₂)₅—NH—CO—O— (trisubstituted benzene) —CO—O—Fe(III)/3 (6) | 0.025 | 13.8 |
| | 0.01 | 18.8 |
| | 0.005 | 25.0 |
| | 0.0025 | 37.5 |
| NC—(CH₂)₅—NH—CO—O— (trisubstituted benzene) —CO—O—Fe(II)/2 (7) | 0.025 | 6.3 |
| | 0.01 | 6.3 |
| | 0.005 | 18.8 |

Table 3-continued

Shoot treatment test/cereal rust/protective

| Active compounds | Active compound concentration in the spray liquor in % by weight | Infection in % of the untreated control |
| --- | --- | --- |
| 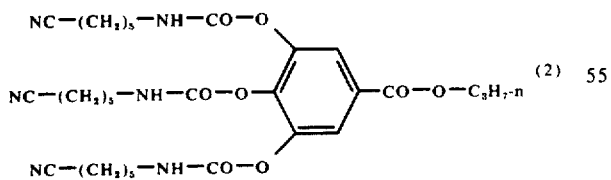 | 0.01<br>0.005<br>0.0025 | 0.0<br>0.0<br>25.0 |

The process according to the present invention is illustrated by the following Preparative Examples:

EXAMPLE 4

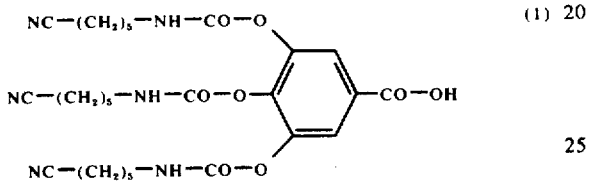

1,560 g (11.3 moles) of δ-cyanopentyl isocyanate were added over the course of 30 minutes to 604 g (3.55 moles) of anhydrous gallic acid, 2.4 l of methylene chloride and 403 g (4 moles) of triethylamine, while cooling. The reaction mixture was dept at about 50° C for 7 hours. It was cooled with ice; ice and water as well as 3 l of methylcyclohexane were added to the reaction mixture, and 258 g of sulphuric acid, diluted with 500 ml of water, were added slowly while stirring well. The reaction product precipitated and became crystalline after some time. It was filtered off and subsequently washed with ice water, to which a small amount of a wetting agent had been added, as well as with methylcyclohexane. The product was dried in vacuo (at about 2 mm Hg), first at room temperature and then at about 55° C. The compound, which was soluble in acetone or acetonitrile, could be recrystallized from an ethyl acetate/toluene mixture; the melting point was about 158° C. IR spectra (KBr): 3,345, 2,245 and 1,745 cm$^{-1}$. The yield was 2,020 g of tris-(N-ω-cyanopentyl-carbamoyl)-gallic acid, that is to say 97% of theory.

EXAMPLE 5

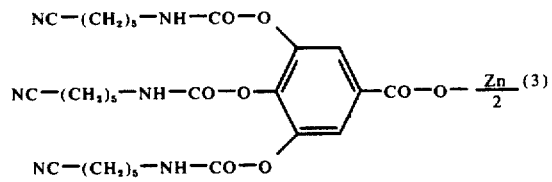

21.2 g (0.1 mole) of gallic acid propyl ester, 44 g (0.32 mole) of ω-cyanopentyl isocyanate and 0.02 g of tin 2-ethylhexanoate were kept at 90° C for 16 hours. On stirring with anhydrous xylene, the melt crystallized. The crystals were treated with dibutyl ether and dried at 50° C/0.1 mm Hg. 56.5 g of tris-(N-ω-cyanopentyl-carbamoyl)-gallic acid propyl ester, that is to say 90% of theory, were obtained. The compound, when recrystallized from an ethyl acetate/dibutyl ether mixture, melted at 80° C (melting point of the crude product was 65°-73° C).

EXAMPLE 6

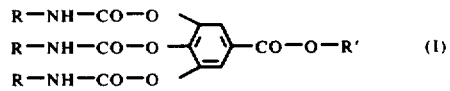

71 of methylene chloride, 1,000 g of ice and 2,000 g (3.4 moles) of tris-(N-ω-cyanopentyl-carbamoyl)-gallic acid (obtained according to Example 4) were first introduced into the reaction vessel, with external cooling. Thereafter, 494 g (1.72 moles) of zinc sulphate heptahydrate, dissolved in 600 g of water, were first added, followed by slow addition of a solution of 138 g (3.45 moles) of sodium hydroxide in 600 g of water. The mixture was further stirred for a period of about 45 minutes, whereby a pH value of 5.5 to 6.4 was reached. The methylene chloride solution was siphoned off and dried twice with sodium sulphate. The filtered solution was concentrated by evaporation in vacuo, until a highly viscous mass had been produced, which was then subsequently dried under greatly reduced pressure at 50° C. 1,924 g of zinc tris-(N-ω-cyanopentyl-carbamoyl)-gallate (that is to say 92% of theory) were obtained as a brittle mass which was soluble in methylene chloride and in an acetone/water mixture in the ratio of 20:1. Spectra: IR (KBr) 3,340-3,380, 2,245 and 1,745-1,755 cm$^{+1}$; IR(CH$_2$Cl$_2$) 3,350-3,370, 3,440, 2,250 and 1,750 cm$^{-1}$.

The following compounds of the formula $$\begin{array}{c} R-NH-CO-O \\ R-NH-CO-O \\ R-NH-CO-O \end{array} \!\!\!\!\bigcirc\!\!\!\!-CO-O-R' \quad (I)$$

were also prepared by procedures analogous to those in the above Examples 4 to 6:

Table D

| Compound No. | R | R' | Properties, metal analysis |
| --- | --- | --- | --- |
| 4 | CH$_3$ | H | Melting point 165° C |
| 5 | n-C$_4$H$_9$ | H | Melting point 181.5° C |

Table D-continued

| Compound No. | R | R' | Properties, metal analysis |
|---|---|---|---|
| 6 | NC—(CH$_2$)$_5$ | Fe(III)$_{/3}$ | IR(KBr): 3,340, 2,245 and 1,745 cm$^{-1}$<br>Fe found: 2.8%; calculated: 3.09% |
| 7 | NC—(CH$_2$)$_5$ | Fe(II)$_{/2}$ | IR(KBr): 3,340, 2,245 and 1,745 cm$^{-1}$<br>Fe found: 4.4%; calculated: 4.57% |
| 8 | NC—(CH$_2$)$_5$ | Sn(II)$_{/2}$ | IR(KBr): 3,340, 2,245 and 1,745 cm$^{-1}$<br>Sn found: 9.6%; calculated: 9.23% |
| 9 | NC—(CH$_2$)$_5$ | Mn(II)$_{/2}$ | IR(KBr): 3,340, 2,245 and 1,745 cm$^{-1}$ |

Other compounds which can be similarly prepared include:

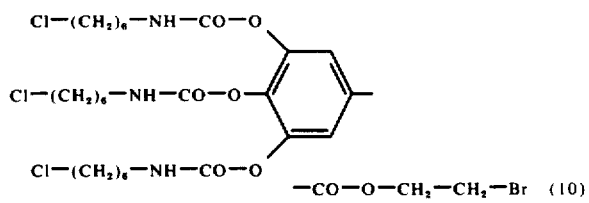
—CO—O—CH$_2$—CH$_2$—Br  (10)

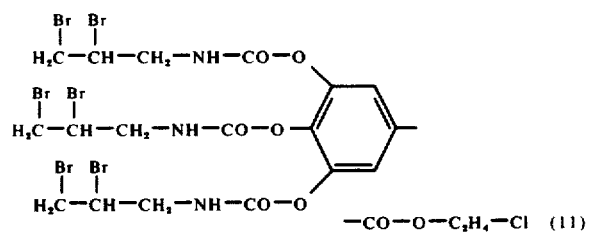
—CO—O—C$_2$H$_4$—Cl  (11)

and the like.

It will be appreciated that the instant specification and examples are set forth by way of illustration and not limitation, and that various modifications and changes may be made without departing from the spirit and scope of the present invention.

What we claim is:

1. A carbamic acid ester of gallic acid, its ester or heavy metal salt, of the formula

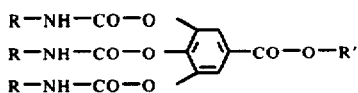

in which
R is alkyl with up to 8 carbon atoms optionally substituted by halogen or cyano, and
R' is hydrogen, optionally halogen-substituted alkyl with up to 6 carbon atoms or one equivalent of a heavy metal atom.

2. A compound according to claim 1 in which R is alkyl with up to 6 carbon atoms optionally substituted by cyano or chlorine, and R' is hydrogen, straight-chain or branched alkyl with up to 6 carbon atoms optionally carrying up to 3 substituents selected from fluorine and chlorine atoms, or one equivalent of a zinc(II), tin(II), manganese(II), iron(II), iron(III), cobalt(II) or nickel-(II) atom.

3. The compound according to claim 1 wherein such compound is tris-(N-ω-cyanopentyl-carbamoyl)-gallic acid of the formula

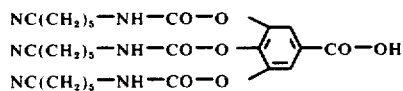

4. The compound according to claim 1 wherein such compound is tris-(N-ω-cyanopentyl)-carbamoyl)-gallate of the formula

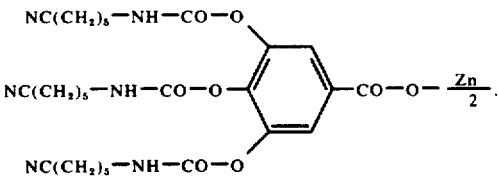

5. A fungicidal composition containing as active ingredient a fungicidally effective amount of a compound according to claim 1 in admixture with a solid or liquefied gaseous diluent or carrier or in admixture with a liquid diluent or carrier containing a surface-active agent.

6. A method of combating fungi which comprises applying to the fungi or a fungus habitat a fungicidally effective amount of a compound according to claim 1.

7. A method according to claim 6 in which said compound is tris-(N-ω-cyanopentyl-carbamoyl) gallic acid.

8. A method according to claim 6 in which said compound is zinc tris-(N-ω-cyanopentyl)-carbamoyl)-gallate.

* * * * *